United States Patent
Willard

[19]

[11] Patent Number: 5,851,176
[45] Date of Patent: Dec. 22, 1998

[54] PRESSURE-RESPONSIVE LOCKOUT VALVE AND METHOD OF USE

[75] Inventor: Steven N. Willard, Minneapolis, Minn.

[73] Assignee: Mentor Corporation, Santa Barbara, Calif.

[21] Appl. No.: 681,859

[22] Filed: Jul. 29, 1996

[51] Int. Cl.⁶ ..................................................... A61F 2/26
[52] U.S. Cl. ............................................................. 600/40
[58] Field of Search ........................ 600/38–41; 128/899; 604/7–10; 623/11, 12; 137/907, 493.6, 493.9; 251/342, 347, 348

[56] References Cited

U.S. PATENT DOCUMENTS

| | | |
|---|---|---|
| 3,683,901 | 8/1972 | Wegener . |
| 3,853,122 | 12/1974 | Strauch et al. . |
| 3,954,102 | 5/1976 | Buuck . |
| 4,009,711 | 3/1977 | Uson . |
| 4,201,202 | 5/1980 | Finney et al. . |
| 4,222,377 | 9/1980 | Burton .............................. 600/38 X |
| 4,310,016 | 1/1982 | Aubel ................................. 137/907 |
| 4,342,308 | 8/1982 | Trick . |
| 4,353,360 | 10/1982 | Finney et al. . |
| 4,383,525 | 5/1983 | Scott et al. . |
| 4,399,811 | 8/1983 | Finney et al. . |
| 4,404,968 | 9/1983 | Evans, Sr. . |
| 4,407,278 | 10/1983 | Burton et al. . |
| 4,412,530 | 11/1983 | Bruton . |
| 4,437,457 | 3/1984 | Trick et al. . |
| 4,441,491 | 4/1984 | Evans, Sr. . |
| 4,537,183 | 8/1985 | Fogarty . |
| 4,550,720 | 11/1985 | Trick . |
| 4,558,693 | 12/1985 | Lash et al. . |
| 4,559,931 | 12/1985 | Fischell . |
| 4,566,446 | 1/1986 | Fogarty . |
| 4,574,792 | 3/1986 | Trick . |
| 4,590,927 | 5/1986 | Porter et al. . |
| 4,596,242 | 6/1986 | Fischell . |
| 4,664,100 | 5/1987 | Rudloff . |
| 4,671,261 | 6/1987 | Fischell . |
| 4,682,583 | 7/1987 | Burton et al. . |
| 4,724,830 | 2/1988 | Fischell . |
| 4,726,360 | 2/1988 | Trick et al. . |
| 4,773,403 | 9/1988 | Daly . |
| 4,782,826 | 11/1988 | Fogarty . |
| 4,829,990 | 5/1989 | Thuroff et al. . |
| 4,917,110 | 4/1990 | Trick . |
| 5,062,416 | 11/1991 | Stucks . |
| 5,062,417 | 11/1991 | Cowen . |
| 5,063,914 | 11/1991 | Cowen . |
| 5,067,485 | 11/1991 | Cowen . |
| 5,101,813 | 4/1992 | Trick ......................................... 600/40 |
| 5,141,509 | 8/1992 | Burton et al. ............................. 623/11 |
| 5,167,611 | 12/1992 | Cowan .................................... 600/40 |
| 5,171,272 | 12/1992 | Levins ..................................... 623/12 |
| 5,250,020 | 10/1993 | Bley ........................................ 600/40 |
| 5,344,388 | 9/1994 | Maxwell et al. ......................... 600/40 |

FOREIGN PATENT DOCUMENTS

43798/85  6/1985  Australia .

*Primary Examiner*—John P. Lacyk
*Assistant Examiner*—Samuel Gilbert
*Attorney, Agent, or Firm*—Fish & Richardson P.C., P.A.

[57] ABSTRACT

A lockout valve for an inflatable penile prosthesis which responds to internal fluid pressure. The lockout valve comprises a housing having inlet and outlet ports, an interior chamber, an apertured valve seat, and a poppet biased toward the closed position. The inlet communicates with the prosthesis reservoir, and the outlet communicates with the interior chamber and the prosthesis pump. The housing includes a flexible diaphragm which moves toward the poppet when flexed inwardly.

Fluid pressure through the inlet port urges the poppet into sealing engagement against the valve seat, therefore closing the lockout valve. Negative fluid pressure applied to the interior chamber from the outlet port (when the pump is actuated) causes the diaphragm to flex inwardly and contact the poppet to open the valve. The lockout valve operates like a check valve when subject to reverse flow.

44 Claims, 3 Drawing Sheets

PRESSURE-RESPONSIVE LOCKOUT VALVE AND METHOD OF USE

BACKGROUND OF THE INVENTION

1. Field of the Invention

This invention relates generally to lockout valves for implantable penile prostheses, and particularly to a valve assembly which responds to an internal pressure differential within the prosthesis and which may be retrofitted to an existing implanted prosthesis.

2. Content of the Prior Art

Implantable penile prostheses for treating impotence are well know to the art. These prostheses generally include a reservoir of biocompatible liquid such as physiological saline implanted within the patient's abdomen, a pump and valve block located within the patient's scrotum, and a pair of cylinders which are implanted within the corpus cavernosae of the penis. Actuating the pump transfers fluid from the reservoir to the cylinders causing them to inflate, thus producing an erection. When the patient wishes to return to a tumescent or flaccid state, he releases the fluid from the cylinders back into the reservoir, in some cases by manually compressing the cylinders to force fluid back to the reservoir. Some representative examples of these penile prostheses and their components or variations are shown in several United States Patents to Buuck '102, Cowen '611, '417, '485, and '914, Fogarty '446, 183, and '826, Bley '020, Uson '711, and Strauch '122, which are incorporated herein by reference.

A wide variety of embodiments of such penile prostheses are known, including the representative examples mentioned above. For example, some prostheses do not utilize a pump, but rather rely on physical compression of the reservoir or a pressurized reservoir to inflate the cylinders. While some prostheses locate the reservoir or pump subcutaneously within the patient's abdomen, others provide a unitary pump and reservoir located within the patient's scrotum. For purposes of this disclosure, many of these prostheses may be considered substantially interchangeable to the extent they include a reservoir, pump, and cylinders (or their structural or functional equivalents).

As noted, one of the components of many prostheses is a valve block, which contains one or more check valves regulating the flow of fluid between the reservoir and cylinders. These check valves prevent the flow of fluid in one direction, and may be spring-biased to remain in a closed position preventing flow in the forward direction until sufficient internal pressure is exerted on the valves to cause them to open. In some embodiments, the check valves are actually palpitatable valves which must be physically manipulated (such as by actuating the pump or squeezing the valve element) in order to open the valve to forward flow.

Another component is a release or relief valve, which serves to permit reverse flow from the cylinders to the reservoir when the release valve is selectively actuated by the patient. The release valve is usually located in the pump or valve block, between the pump and the cylinders, or within or near the cylinders.

While the check valves and release valves are suitable to selectively control the flow of fluid between the reservoir and the cylinders during normal operation, it was soon recognized that pressure exerted on the reservoir during physical activity or movement by the patient could cause the inadvertent and undesired inflation of the cylinders. If sufficient pressure is placed on the reservoir (for example, when a patient who has an abdominal reservoir bends over, or a patient having a scrotal reservoir sits down or crosses his legs), the pressure on the reservoir may overcome the resistance of the spring-biased check valve, causing complete or partial inflation of the cylinders. In prostheses having pressurized reservoirs, the unintended activation of the control valve can produce the same result. In the event of accidental auto-inflation—either partial or total—the patient would be required to manually open the release valve and physically compress the cylinders to deflate them.

In addition, encapsulation or calcification frequently occurs around the reservoir. This can lead to more frequent instances of auto-inflation (since the capsule may transmit or focus more pressure on the reservoir when the patient moves or bends), or result in continuous partial inflation because the capsule exerts pressure on the reservoir that overcomes the check valve or prevents complete deflation of the cylinders.

As may be readily appreciated, instances of accidental auto-inflation can be quite embarrassing and painful for a patient, and may restrict their ability to engage in certain recreational or daily activities. In addition, even for patients whose actual incidents of accidental auto-inflation might be infrequent, the mere risk of such an occurrence may cause them to refrain from activities in which they might otherwise engage.

Lockout valves to prevent auto-inflation of the chambers are therefore well known to the art. As meant herein, the term "lockout valve" means a valve or flow control other than the check or release valves, which serves to prevent accidental auto-inflation and is characterized by requiring selective actuation or activation by the patient in order to permit fluid flow in the positive direction (i.e., from the reservoir to the cylinders), and which will remain closed despite high fluid pressures experienced by or exerted from fluid in the reservoir or connecting tubing.

Conventional lockout valves include those which are normally-closed (returning to a completely closed position when not being manually actuated) versus bi-stable (having distinct open and closed positions in which the valve will remain until manually moved to the contrary position).

Representative examples of various lockout valves are shown in several United States and foreign patents, the disclosures of which are incorporated herein by reference.

The Cozzi '798 patent application discloses a prostheses having an abdominal reservoir with either a palpitatable or bi-stable "spigot" type lockout valve located in the scrotum. The Cozzi '798 patent does not utilize a pump, but instead relies on manual compression of the reservoir. The Trick '110 patent shows a bi-stable lever-type valve mounted on a pressurized reservoir located within the scrotum. The Stucks '416 patent provides bi-stable valves associated with each cylinder which control both inflation and deflation.

The Evans '491 and '968 patents disclose bi-stable crossover valves which are connected in line between the pump and cylinders. The Burton '509 patent discloses an embodiment having a bi-stable valve located in the valve block, and an embodiment in which the valve actuator is located inside the pump bulb.

The Daly '403 and Trick '360 patents disclose palpitatable valves which are formed integrally with the pump and are therefore located within the patient's scrotum. The Lash '693 patent shows a palpitatable valve disposed slightly downstream from the unitary pump and reservoir.

The Fischell '242 and '830 patents disclose subcutaneous lockout valves positioned within the patient's abdomen or pubic area, which are opened by depressing a spring-biased plunger or resilient diaphragm.

Although not exhaustive of the various structures and embodiments of lockout valves developed or utilized with inflatable penile prostheses, these examples are believed to represent the basic concepts or methods previously employed by those skilled in the art of designing penile prostheses to prevent accidental auto-inflation.

However, these designs do present or reflect several significant disadvantages or drawbacks.

Several of the lockout valves require two-handed operation—one to actuate the lockout valve, and the other to operate the pump or compress the reservoir. It may also be difficult to initially locate or manipulate the activation mechanisms in some of the lockout valves.

Subcutaneous abdominal lockout valves may become less responsive when implanted due to calcification and the formation of scar tissue, or due to movement within the patient unless the lockout valve is secured to an available anatomical structure.

Some of the lockout valves can cause additional discomfort due to their size or shape, or may expose the patient to the risk of internal injuries or damage due to interference with vesicles or lumen within the scrotum, or as a result of manipulating the valve's actuation mechanism. The size and shape of some lockout valves may increase the complexity or risks associated with the implant procedure itself, or prohibit some types of less invasive surgical procedures.

Finally, some of the valves are unduly complicated or expensive to manufacture, and may be subject to mechanical wear, failure, or rejection that would necessitate repair or replacement, thereby involving additional surgery for the patient.

SUMMARY OF THE INVENTION

The lockout valve of this invention is designed to prevent accidental auto-inflation when fluid pressure from the reservoir exceeds the threshold opening value of the check valves, and yet still provides automatic operation whenever the patient selectively actuates the pump bulb without the need to separately operate the lockout valve.

The lockout valve of this invention provides several additional advantages compared with contemporary designs. It is very small and inexpensive to manufacture. Its components can be fabricated from biocompatible silicone rubber or plastics, and the design does not require high fabrication tolerances. It has relatively few moving parts, and is not as prone to damage or failure due to fatigue or wear. It may be manufactured as an integral component of a penile prosthesis, or retrofitted to a wide variety of existing prostheses (in which the reservoir is spaced apart from the cylinders) using existing tubing and conventional connectors. The lockout valve allows setting a lower threshold pressure for opening the main check valve of the prosthesis, which in turn permits the pump bulb to be activated with less "squeezing" force. The ability to modify the pump bulb and valve block to operate under less external pressure may also allow a release valve which is easier to operate. Since the lockout valve itself does not require manipulation by the patient, it may be located anywhere between the reservoir and pump—such as on the reservoir or in the abdomen—and therefore outside the scrotum. At internal pressures below the threshold value for the prosthesis' check valve, the lockout valve may optionally exhibit a "leaky" characteristic which facilitates maintaining a normal pressure equilibrium between the reservoir and pump as comparably small compressive forces are placed on each, which may not be accomplished using a normally closed or bi-stable lockout valve.

Briefly described, the pressure-responsive lockout valve of this invention consists of a valve body or housing having inlet and outlet ports, with an interior chamber, an apertured valve seat, and a poppet which moves axially relative to that valve seat and aperture. The inlet leads from the reservoir to the side of the valve seat opposing the interior chamber, and the outlet fluidly communicates with the interior chamber and the cylinders. The poppet is normally biased toward or in the closed position by a spring force exerted by a plurality of flexible tines. A portion of the valve body proximate to the interior chamber defines a flexible membrane or diaphragm having an area generally larger than the area of the aperture in the valve seat or the face of the poppet. That diaphragm generally moves toward the poppet and valve seat when flexed inwardly.

In operation, fluid pressure exerted from the reservoir through the inlet port urges the poppet into more positive sealing engagement against the valve seat, therefore closing the lockout valve and preventing fluid in the reservoir from inflating the cylinders. Negative fluid pressure applied to the interior chamber from the outlet port and tubing when the pump is selectively actuated by the patient causes the diaphragm to flex inwardly and contact the poppet. The force exerted on the poppet by the diaphragm will exceed the fluid pressure exerted from the reservoir and the lockout valve will automatically open, thereby permitting fluid in the reservoir to inflate the cylinders. The lockout valve operates like a check valve when subject to reverse flow, so that when the patient opens the release valve on the pump and deflates the cylinders, the positive pressure of the fluid flowing in the reverse direction through the outlet port and into the interior chamber exerts pressure on the poppet which exceeds the spring force exerted by the flexible tines, and the lockout valve opens.

DESCRIPTION OF THE PREFERRED EMBODIMENTS

The fluid pressure-responsive lockout valve for an inflatable penile prosthesis and its method of operation are shown in FIGS. 1–7, and generally referenced therein by the numeral 10. For expedience, the fluid pressure-responsive lockout valve 10 may be referred to herein simply as the lockout valve 10.

Figure 1:
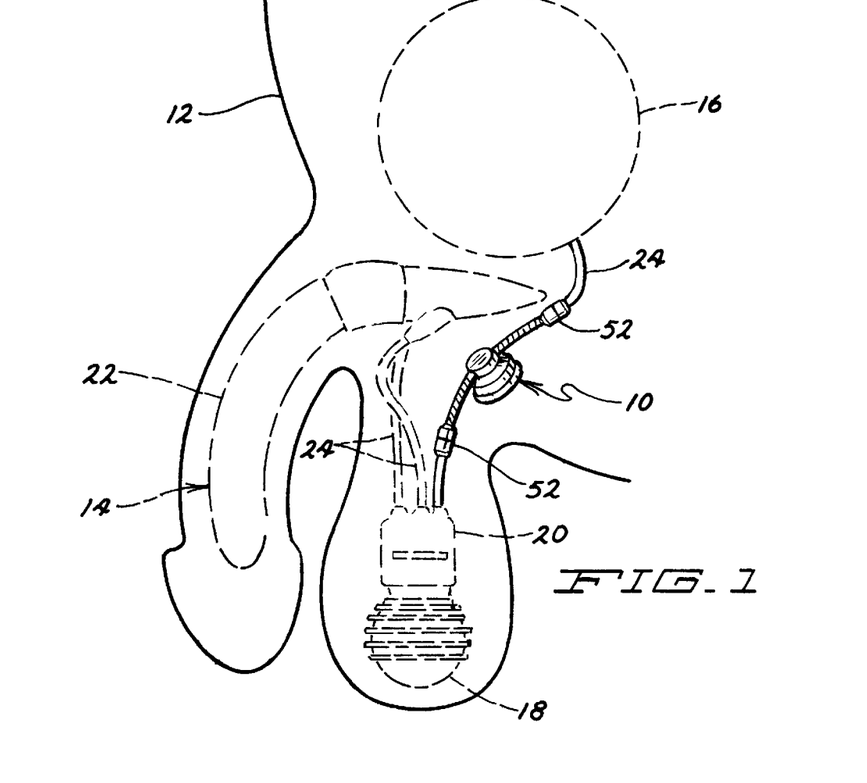
FIG. 1 is a side elevation view of an inflatable penile prosthesis including one embodiment of the pressure-responsive lockout valve of this invention implanted within a male patient.

Referring particularly to FIG. 1, the lockout valve 10 is shown in its anatomical environment within a male patient 12 as a component of an inflatable penile prosthesis 14. The prosthesis 14 includes a remote reservoir 16 located in the abdomen of the patient 12, a pump bulb 18 and unitary valve block 20 located within the scrotum of the patient 12, and a pair of inflatable cylinders 22 each located within the corpus cavernosa of the penis of the patient 12, these components being operatively connected in fluid communication by a plurality of segments of tubing 24. The lockout valve 10 is disposed roughly equidistant between the reservoir 16 and valve block 20. The prosthesis 12 shown herein for exemplary purposes is of the type whose manufacture and use is generally described in greater detail by the Cowen '611, '417, '485, and '914, Fogarty '446, 183, and '826, and Bley '020 patents identified above and incorporated herein by reference as though fully set forth. It is understood that the lockout valve 10 may be utilized with a wide variety of prostheses 12 other than this representative example.

Figure 2:
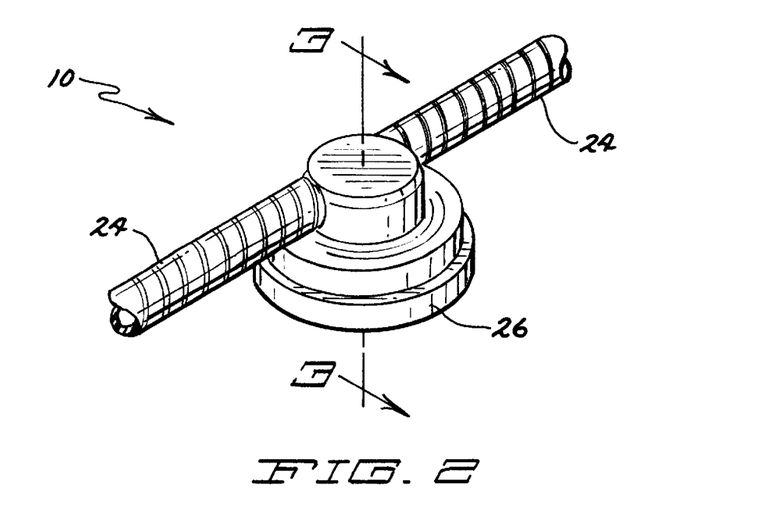
FIG. 2 is a perspective view of the exterior of the pressure-responsive lockout valve of FIG. 1.
Figure 3:
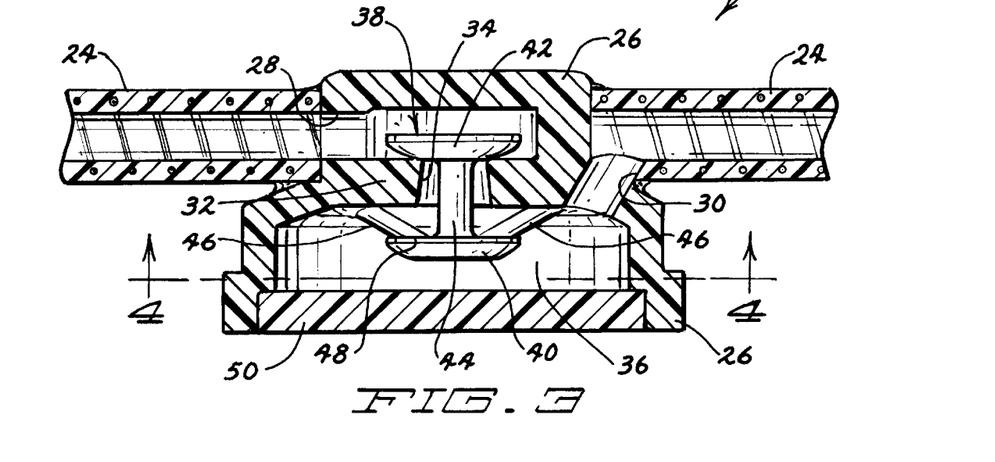
FIG. 3 is a side cross section view of the pressure-responsive lockout valve of FIG. 1 taken through line 3—3 in FIG. 2.
Figure 4:
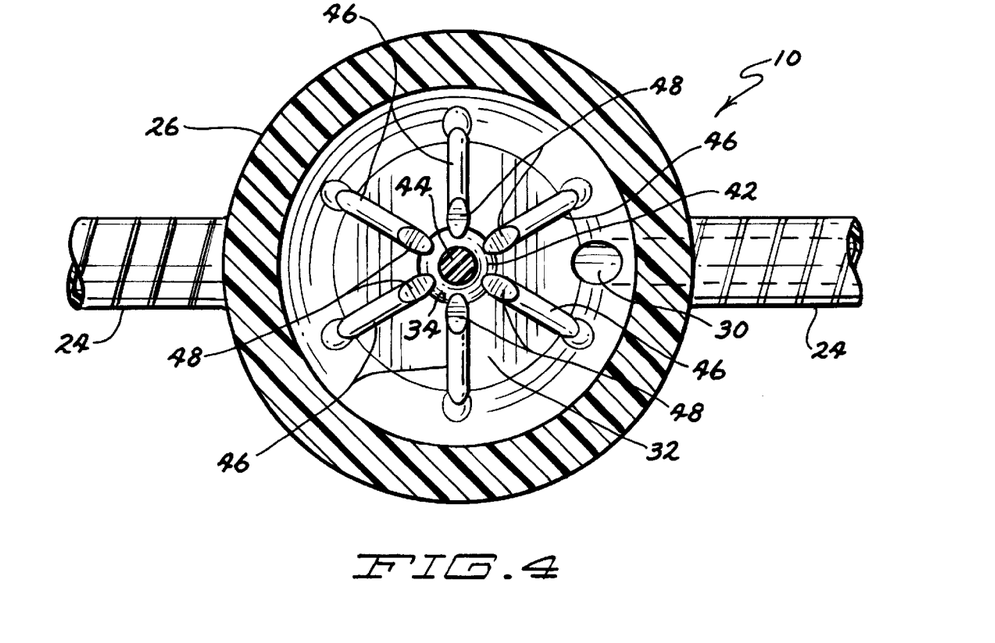
FIG. 4 is a transverse cross section view of the pressure-responsive lockout valve of FIG. 1 taken through line 4—4 of FIG. 3.

Referring particularly to FIGS. 2–4, the structure of one embodiment of the lockout valve 10 is shown in greater detail. The lockout valve 10 includes a housing or body 26 having a generally disk-shaped outer configuration with a plurality of steps or segments, with the body 26 being fluidly connected in line along the tubing 24 such that segments of the tubing extend outwardly in diametrically opposing directions from an inlet port 28 and an outlet port 30 extending through the outer walls of the body 26. The body 26 defines a generally planar valve seat 32 having a central aperture 34. The valve seat 32 and body 26 define an interior chamber 36 which is generally disposed on the opposite side of the valve seat 32 relative to the inlet port 28, but in direct proximity to and fluid communication with the outlet port 30.

A dumbbell-shaped poppet 38 or valve member is disposed or mounted within the aperture 34 of the valve seat 32 so as to move axially therein back and forth relative to the valve seat 32 and interior chamber 36. The poppet 38 includes an enlarged disk-shaped head 40 and tail 42 which are connected by a generally cylindrical shaft 44. The head 40 and tail 42 have diameters sufficiently large to cover and close the entire aperture 34. The shaft 44 has a diameter sufficiently small so that inflation fluid may pass between the shaft 44 and valve seat 32 through the aperture 34, and a length sufficiently great so that the head 40 and tail 42 of the poppet 38 are spaced apart sufficiently that they can simultaneously be displaced from contact with the valve seat 32 on both sides thereof to permit fluid flow through the aperture 34. Concurrently, the valve seat 32 has a sufficient thickness and the shaft 44 a sufficient diameter to prevent the poppet 38 from pivoting out of proper alignment, thereby constraining the axial movement of the poppet 38 to generally parallel alignment with the longitudinal axis of the shaft 44 so the tail 42 of the poppet 38 contacts flush with the confronting planar surface of the valve seat 32.

A plurality of flexible tines 46 spaced around the aperture 34 extend radially inward into the interior chamber 36 from the valve seat 32 in a spoke-like configuration, each of the tines 46 being angled generally acutely away from the valve seat 32. Each tine 46 terminates in a beveled or truncated distal tip 48 disposed axially between the head 40 of the poppet 38 and the valve seat 32, which together define a plane and support the head 40 of the poppet 38 to bias it away from the valve seat 32 into the interior chamber 36. The distal tips 48 of the tines 46 are spaced sufficiently from the shaft 44 so that any two tines 46 on opposing sides of the shaft 44 will not both contact the shaft 44 and prevent further axial movement of the poppet 32 prior to the head 40 of the poppet 38 being moved axially as close to the valve seat 32 (or the tail 42 being moved axially as far away from the valve seat 32) as is desired or required for normal operation of the lockout valve 10.

The body 26 of the lockout valve 10 also defines a generally circular flexible diaphragm 50 or membrane which traverses across the radial extent of the interior chamber 36, the center point of which is generally aligned with the longitudinal axis of the poppet 38 and the aperture 34. The center point of the diaphragm 50 therefore moves toward the head 40 of the poppet 38 along the longitudinal axis when the diaphragm 50 flexes concavely inward into the interior chamber 46, and the diaphragm 50 may also bow convexly outward away from the poppet 38. The relative flexibility or resiliency of the diaphragm 50, its diameter, and its spacing from the poppet 38 and valve seat 32 are such that at its maximum concave inward flexure, the diaphragm 50 contacts the head 40 of the poppet 38 and presses it fully toward the valve seat 32 to the extent permitted by the resiliency of the tines 46 or the physical interjection of the tines 46 between the head 40 of the poppet 38 and the confronting surface of the valve seat 32. The diaphragm 50 may be molded integrally with the body 26, or may be adhered or otherwise attached to the body 26 in applications where the body 26 must initially be left partially open to permit installation of the poppet 38 into the aperture 34 in the valve seat 32. Similarly, the segments of tubing 24 may be molded integrally with the body 26, or may be adhered or attached to the body 26 in fluid communication with the inlet port 28 and outlet port 30.

The poppet 38 is lathed or otherwise fabricated from a more rigid polymer such as polysulfone that is sufficiently rigid to deform or stretch the aperture 34 to permit the head 40 or tail 42 of the poppet 38 to be forcibly pressed through the aperture 34 to mount the poppet 38 relative to the valve seat 32, with the respective head 40 or tail 42 optionally being beveled or tapered to facilitate mounting while preventing inadvertent detachment. The body 26 of the lockout valve 10 may be fabricated from a biocompatible elastomer such as silicone rubber, a plastic or ploymer, or the like, using any conventional molding or fabrication procedure or assembly of separate subcomponents. The particular embodiment of the lockout valve 10 shown in FIGS. 2–4 may be constructed so that the body 26 has to have an overall diameter of approximately 1.0" or less, with a total thickness on the order of 0.5" or less.

It may readily be appreciated that lockout valve 10 of this invention may be fabricated in a variety of embodiments and configurations which are structurally and functionally interchangeable, the preferred embodiment of which has been disclosed in detail herein. In addition, the dimensions, tolerances, and physical characteristics of the materials selected for the lockout valve 10 may be determined based upon the particular application and conditions to which the lockout valve 10 will be subjected, and according to well known principles familiar to those of ordinary skill in designing such components.

Figure 5:
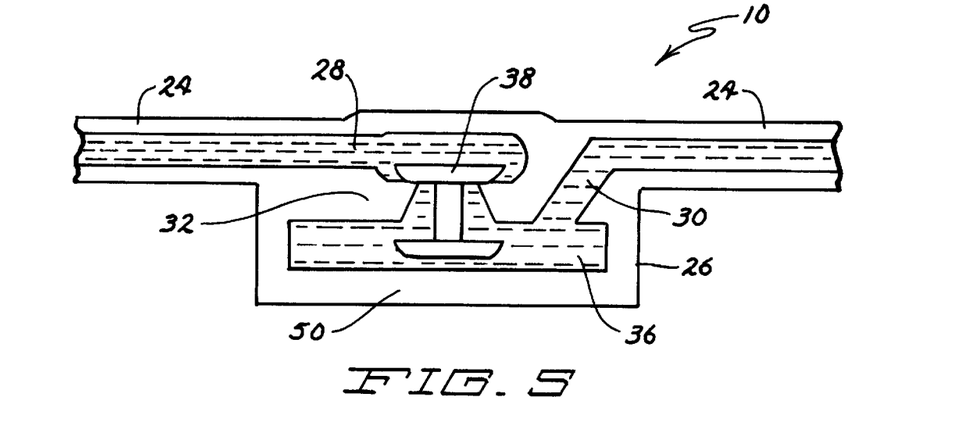
FIG. 5 is a diagrammatic illustration of the pressure-responsive lockout valve of FIG. 1 in the closed position.
Figure 6:
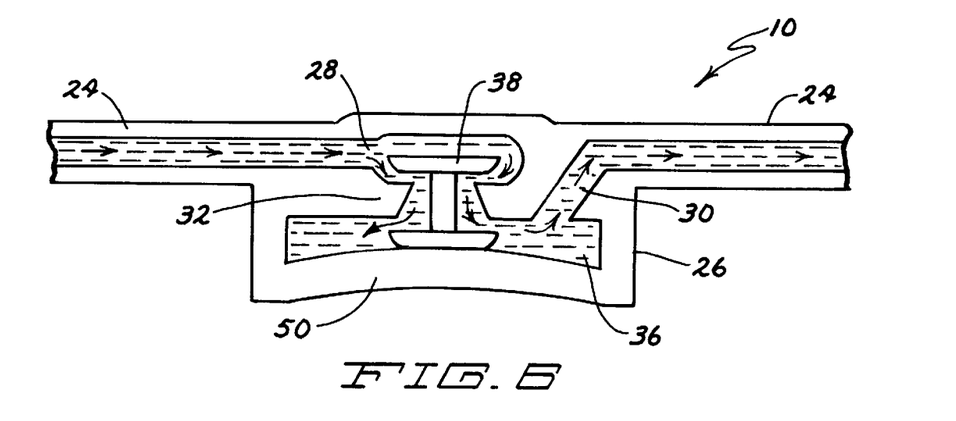
FIG. 6 is a diagrammatic illustration of the pressure-responsive lockout valve of FIG. 1 in the open position due to negative pressure applied on the outlet port.
Figure 7:
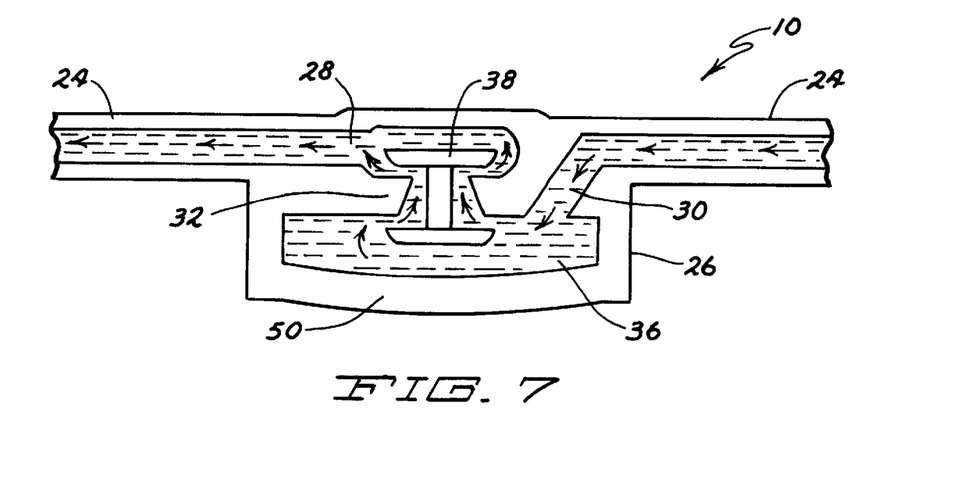
FIG. 7 is a diagrammatic illustration of the pressure-responsive lockout valve of FIG. 1 in the open position due to reverse flow from the outlet port.

The operation of the lockout valve 10 may be further understood with reference particularly to FIGS. 5–7. The lockout valve 10 is connected in line with the reservoir 16 and pump valve block 20 by tubing 24 such that the inlet port 28 is functionally oriented towards and fluidly communicates with the reservoir 16, and the outlet port 30 is functionally oriented towards and fluidly communicates with the valve block 20 or pump bulb 18. In contrast, the spatial orientation of the lockout valve 10, the inlet port 28, and outlet port 30 may be configured or arranged in any manner that is deemed suitable or practical to fabricating the lockout valve 10.

In this configuration, a liquid such as physiological saline or other inflation fluid contained within the reservoir 16 will flow along a path from the reservoir 16 through tubing 24 to the inlet port 28, and through the inlet port 28 into the lockout valve 10 on the side of the valve seat 32 opposing the interior chamber 36. When the aperture 34 is not closed by the tail 42 of the poppet 38, the fluid will continue flowing along a path through the aperture 34 and into the interior chamber 36. When the pump bulb 18 is actuated, a negative pressure (or suction) is exerted on the segment of tubing 24 extending from the valve block 20 or pump bulb 18 to the outlet port 30, that negative pressure acting to draw fluid from the interior chamber 36 through the outlet port 30 and tubing 24 toward the pump bulb 18.

Referring particularly to FIG. 5, if pressure is physically exerted on the reservoir to increase the internal fluid pressure within the reservoir and the tubing 24 connected to the inlet port 28, that internal fluid pressure will cause the tail 42 of the poppet 38 to seat against and form a fluid-tight seal with the confronting face of the valve seat 32. However, it has been found that the biasing force exerted by the tines 46 need not be so strong as to continuously maintain a fluid-tight seal between the poppet 38 and valve seat 32 in the absence of an internal fluid pressure from the reservoir 16 that exceeds the predetermined threshold pressure required to open the check valve in the valve block 20 leading to the cylinders 22. Consequently, at an internal fluid pressure from the reservoir 16 less than the threshold opening pressure for the check valve, the lockout valve 10 may be "leaky" to the extent it is not normally closed or forms a fluid-tight seal. However, once the internal fluid pressure from the reservoir 16 approaches or exceeds the threshold pressure of the check valve, the lockout valve 10 becomes fluid-tight and increasing the internal fluid pressure from the reservoir 16 increases the integrity of that seal.

When the pump bulb 18 is selectively actuated by the patient 12, the pump bulb 18 creates a negative internal fluid pressure within the tubing 24 and interior chamber 36. This negative internal fluid pressure or vacuum force causes the diaphragm 50 to flex concavely inward into the interior chamber 36, to a point at which the diaphragm 50 contacts the head 40 of the poppet 38 and moves the poppet 38 axially to displace the tail 42 from the valve seat 32 as shown particularly in FIG. 6, thereby opening the lockout valve 10 and permitting inflation fluid to flow from the reservoir 16 along a path through the tubing 24, inlet port 28, aperture 34, interior chamber 36, outlet port 30, and tubing 24 to the valve block 20 and pump bulb 18.

It may further be appreciated that a proper functional balance must be established between the internal fluid pressure exerted by the reservoir 16, the biasing force of the tines 46, and the negative internal fluid pressure resulting in the interior chamber 36 created by the pump bulb 18. The pressure differential within the system would normally require a fluid pressure from the reservoir 16 that is less than the negative pressure exerted by the pump bulb 18 in order for the lockout valve 10 to open during use. However, the relatively large size of the diaphragm 50 compared to the relatively small diameters of the aperture 34 and the contact area between the tail 42 of the poppet 38 and the valve seat 32 provides a sufficient mechanical advantage which ensures that a moderate negative internal pressure exerted by the pump bulb 18 will overcome a significantly greater internal pressure created by compressing the reservoir 16, but only when the pump bulb 18 has been selectively actuated by the patient 12. Absent actuation of the pump bulb 18 or a negative internal pressure created by the pump bulb 18, the poppet 38 is biased to its closed position (both by any internal pressure from the reservoir 16 and the spring force of the tines 46), and a fluid-tight seal is formed with the valve seat 32. As such, the relevant criteria are the proportionate forces exerted on the poppet 38 due to the hydrodynamic forces on the diaphragm 50 and poppet 38, the resulting mechanical force exerted by the diaphragm 50 on the poppet 38, and the comparably small mechanical spring force exerted by the tines 46.

The lockout valve 10 will remain in the sealed closed position until the internal pressure from the reservoir 16 drops sufficiently below a predetermined value which is characteristic to the lockout valve 10, and which is below the threshold pressure required by the check valve, at which point the lockout valve 10 may be permitted to exhibit the "leaky" characteristic. The "leaky" characteristic of the lockout valve 10 is not believed to be necessary to the proper functioning of the lockout valve 10, but in situations where the pump bulb 18 may be inadvertently compressed a small amount, the check valve will prevent auto-inflation of the cylinders 22 while the slight increase in internal pressure will be absorbed by the reservoir 16 and may then be retransmitted back to the pump bulb 18 through the lockout valve 10 when the compression is released, thus maintaining a normal equilibrium between the reservoir 16 and pump bulb 18 without a risk of inadvertent auto-inflation of the cylinders 22. A normally closed or bi-stable lockout valve 10 that maintains a fluid-tight seal would not permit this operation.

As noted, the lockout valve 10 operates in a manner similar to a check valve when subject to reverse flow, as shown in FIG. 7. When the patient activates the release valve (not shown) in the valve block 20 to permit deflation of the cylinders 22, the increased internal pressure created by manually compressing the cylinders 22 causes increased internal pressure within the interior chamber 36. The diaphragm 50 will bow convexly away from the poppet 38, and the internal fluid pressure within the interior chamber 36 will exerting force on the tail 42 of the poppet 38 which overcomes the biasing force of the tines 46, thus opening the lockout valve 10 and permitting the inflation fluid to flow in the reverse direction through the lockout valve and thus refilling the reservoir 16.

Referring again to FIG. 1, it may be seen that in addition to fabricating the lockout valve 10 as a standard component of an assembled prosthesis 14 prior to initial implantation within a patient 12, the lockout valve 10 may also be designed to permit retrofitting to an existing implanted prosthesis 14.

In order to retrofit the lockout valve 10 to an existing prosthesis 14, the lockout valve 10 is fabricated with a short segment of tubing 24 extending from each of the inlet port 28 and outlet port 30, with each segment having a free end. An intermediate section of the tubing 24 between the reservoir 16 and valve block 20 or pump bulb 18 is cut or removed to produce two free exposed ends, and the lockout valve 10 is then spliced into that tubing 24 using a pair of mating connectors 52 of any conventional and suitable type available. The lockout valve 10 may be fabricated with the free ends of the segments of tubing 24 having one half of each pair of mating connectors 52 already attached, or the operator may attach the mating connectors 52 to all four free ends of the tubing during the retrofit procedure. It may be appreciated that in the case of retrofitted lockout valves 10, the segments of tubing 24 or the lockout valve 10 should be color coded or marked with a visible or tactile indicia such as arrows that ensure the operator will properly orient and connect the lockout valve 10 with that the inlet port 28 disposed functionally towards the reservoir 16 and the outlet port 30 disposed functionally towards the valve block 20 and pump bulb 18.

While the lockout valve 10 of this invention was conceived and designed for the purpose of providing an optimal solution to the problem of accidental auto-inflation of an inflatable penile prosthesis 13 as described above, it may be readily appreciated that this lockout valve 10 could be utilized successfully in other applications relating to other medical devices or products unrelated to the treatment of medical dysfunction.

One representative example in the field of medical devices would be an intravenous (IV) line used for the introduction of fluid medication to a patient. In a standard non-gravity IV line, a pump draws fluid from a reservoir such as an IV bag under vacuum, and pumps the fluid through a catheter or IV tube under pressure into the patient at a carefully metered rate. In some systems, if the IV line is detached from the pump or the pump is stopped—and the IV line is not manually closed by a valve—the IV fluid or medication may continue draining or being drawn into the patient at an unmetered rate, resulting in overmedication. Placement of a lockout valve 10 of the type disclosed herein between the IV pump and the IV bag will automatically terminate the flow from the IV bag in the event the negative pressure from the pump is interrupted.

A related example would be an arterial catheter used for injecting or withdrawing fluids from a patient. The lockout valve placed along the catheter between the injection site and the patient would prevent blood flowing through the catheter from the patient except when a syringe or hemotube is attached to the catheter and providing a source of negative pressure to withdraw a sample. The lockout valve would act as a check valve when administering medication or injecting fluids through the catheter.

It is also appreciated that various embodiments of the lockout valve 10 may be developed which utilize the inventive concept disclosed herein of a lockout valve 10 for a penile prosthesis 14 which responds to internal fluid pressures (static or dynamic) within the prosthesis 14 but which operate in different manners or modes. For example, in a system having a check valve in the valve block 20, a subjectively less desirable but workable embodiment of the lockout valve 10 could be fabricated having a distinct section of tubing 24 extending from the valve block 20 or pump bulb 20 to carry inflation fluid under positive pressure back to the lockout valve 10 when the pump bulb 18 is actuated, with that positive pressure from the inflation fluid in the segment of tubing 24 acting on the valve member or poppet 38 (with the benefit of any necessary mechanical advantage or leverage) to open the lockout valve 10. Alternately, a lockout valve 10 could be fabricated which responds to momentary fluid back-pressure created when the pump bulb 18 is actuated, however such a system would impose significant complexity in balancing the respective activation pressures for the lockout valve 10 and check valve.

While representative examples of the preferred embodiments of the above fluid pressure-responsive lockout valve 10 have been described in detail with reference to the attached drawing Figures, it is understood that various changes, adaptations, and modifications may be made in the fluid pressure-responsive lockout valve 10 and its method of fabrication and use without departing from the spirit and scope of the following appended claims.

What is claimed is:

1. In a prosthesis having a reservoir, a pump, an inflatable component, and an inflation fluid, said pump being selectively actuated by a user to inflate the inflatable component with said inflation fluid supplied from said reservoir, the improvement comprising:

a fluid pressure-responsive lockout valve disposed between and operatively connected to both the reservoir and the inflatable component in fluid communication therewith to prevent inadvertent auto-inflation of the inflatable component, said fluid pressure-responsive lockout valve including an inlet port, an outlet port, a valve member, a valve seat, a valve body defining an interior chamber in fluid communication with the outlet port, and a diaphragm, wherein the valve member includes a poppet, and the valve seat defines an aperture, said valve member being movable between a closed position in sealing contact with said valve seat and an open position, said inlet port connected in fluid communication with the reservoir and said outlet port connected in fluid communication with the pump, such that when the pump is selectively actuated by the user to produce a negative internal fluid pressure at said outlet port, the diaphragm flexes inwardly into the interior chamber causing the diaphragm to contact the poppet and open the aperture, thereby permitting the inflation fluid to flow from the reservoir through said fluid pressure responsive lockout valve to the inflatable component.

2. The improvement of claim 1 wherein the poppet moves axially relative to the valve seat generally parallel to a longitudinal axis, and the diaphragm is generally circular having a center point, said center point being generally aligned with said longitudinal axis along which the poppet moves axially.

3. The improvement of claim 1 wherein the poppet has a head, a tail, and a shaft, said head and said tail each being disposed on opposing ends of said shaft and opposing sides off the valve seat such that said shaft extends at least partially through the aperture, said tail of the poppet confrontingly contacting the valve seat and sealing the aperture when the poppet is in the closed position.

4. The improvement of claim 1 wherein the poppet has a head, a tail, and a shaft, said head and said tail each being disposed on opposing ends of said shaft and opposing sides of the valve seat such that said shaft extends at least partially through the aperture, the lockout valve including a bias member that exerts a bias force to bias said head of the poppet away from the valve seat.

5. The improvement of claim 4 wherein the bias member includes a plurality of flexible tines that exert the spring force on the head of the poppet, the flexible tines extending from the valve body and contacting the head of the poppet.

6. The improvement of claim 1 wherein the lockout valve includes a bias member that exerts a spring force to bias the poppet toward the closed position.

7. The improvement of claim 6 wherein the bias member includes a plurality of flexible tines extending from the valve body and contacting the poppet.

8. The improvement of claim 1 wherein the lockout valve includes a bias member that exerts a spring force to bias the valve member toward the closed position.

9. The improvement of claim 1 wherein the prosthesis includes a valve block having a check valve which opens at a predetermined threshold fluid pressure, and wherein the fluid pressure-responsive lockout valve permits the flow of fluid through the valve seat in a forward direction when fluid pressure from the reservoir is sufficiently less than said predetermined threshold fluid pressure, and the valve member moves to the closed position in sealing engagement with the valve seat at least when fluid pressure from the reservoir increases to said predetermined threshold fluid pressure.

10. The improvement of claim 1 wherein the reservoir, the pump, and the inflatable component are operatively connected to one another in series, and wherein the fluid pressure-responsive lockout valve is disposed between the reservoir and the pump.

11. The improvement of claim 10 wherein the reservoir is operatively connected to the pump via a tubing, and the fluid pressure-responsive lockout valve is operatively connected to said tubing for fluid communication therewith.

12. The improvement of claim 1 wherein the fluid pressure-responsive lockout valve includes a valve body and wherein at least said valve body and the valve seat are fabricated from an elastomer.

13. A lockout valve for use with a penile prosthesis having a reservoir, a pump, an inflatable cylinder, and an inflation fluid, said pump being selectively actuated by a user to inflate said inflatable cylinder with said inflation fluid, said lockout valve being disposed between and operatively connected to said reservoir and said inflatable cylinder in fluid communication therewith, said lockout valve preventing inadvertent auto-inflation of said inflatable cylinder, said lockout valve comprising:

a valve body defining an inlet port and an outlet port, an interior chamber in fluid communication with the outlet port, and a movable surface, a valve seat disposed on said valve body;

and a valve member mounted for movement relative to the valve seat, said valve member being movable between a closed position in sealing contact with said valve seat and an open position, said inlet port connectable in fluid communication with the reservoir, said outlet port connectable in fluid communication with a pump, such that when the pump is selectively actuated by the user to produce a negative internal fluid pressure at the outlet port of the lockout valve, the movable surface moves inwardly into said interior chamber, causing the surface to contact the valve member, causing the valve member to move to the open position and permitting the inflation fluid to flow from the reservoir through the lockout valve to the inflatable cylinder.

14. The lockout valve of claim 13 wherein the movable surface includes a flexible diaphragm, the valve member includes a poppet, and the valve seat defines an aperture, said diaphragm flexing inwardly into said interior chamber when the negative internal pressure is applied at the outlet port causing said diaphragm to contact said poppet and open said aperture, thereby permitting the inflation fluid to flow from the inlet port through said aperture in the valve seat, said interior chamber, and said outlet port.

15. The lockout valve of claim 14 wherein the poppet moves axially relative to the valve seat generally parallel with a longitudinal axis, and the diaphragm is generally circular having a center point, said center point being generally aligned with said longitudinal axis along which the poppet moves axially.

16. The lockout valve of claim 14 wherein the poppet has a head, a tail, and a shaft, said head and said tail each being disposed on opposing ends of said shaft and opposing sides of the valve seat such that said shaft extends at least partially through the aperture, said tail of the poppet confrontingly contacting the valve seat and sealing the aperture when the poppet is in the closed position.

17. The lockout valve of claim 14 wherein the poppet has a head, a tail, and a shaft, said head and said tail each being disposed on opposing ends of said shaft and opposing sides of the valve seat such that said shaft extends at least partially through the aperture, the lockout valve including a bias member that exerts a spring force to bias said head of the poppet away from the valve seat.

18. The lockout valve of claim 17 wherein the bias member includes a plurality of flexible tines extending from the valve body and contacting the head of the poppet.

19. The lockout valve of claim 14 wherein the lockout valve includes a bias member that exerts a spring force to bias the poppet toward the closed position.

20. The lockout valve of claim 19 wherein the bias member includes a plurality of flexible tines extending from the valve body and contacting the poppet.

21. The lockout valve of claim 13 wherein the lockout valve includes a bias member that exerts a spring force to bias the valve member toward the closed position.

22. The lockout valve of claim 13 wherein the penile prosthesis includes a valve block having a check valve which opens at a predetermined threshold fluid pressure, and wherein the lockout valve permits the flow of fluid through the valve seat in a forward direction when fluid pressure from the reservoir is sufficiently less than said predetermined threshold fluid pressure, and the valve member moves to the closed position in sealing engagement with the valve seat at least when fluid pressure from the reservoir increases to said predetermined threshold fluid pressure.

23. The lockout valve of claim 13 wherein the reservoir, the pump, and the inflatable cylinder are operatively connected to one another in series, and wherein the lockout valve is disposed between the reservoir and the pump.

24. The lockout valve of claim 23 wherein the reservoir is operatively connected to the pump via a tubing, and the pressure-responsive lockout valve is operatively connected to said tubing for fluid communication therewith.

25. The lockout valve of claim 13 wherein the valve body and the valve seat are fabricated from an elastomer.

26. The lockout valve of claim 13 wherein at least the valve member is fabricated from a plastic.

27. A method for retrofitting a lockout valve to a penile prosthesis, said penile prosthesis having a reservoir, a pump, an inflatable cylinder, a conduit extending between and fluidly communicating with said reservoir said inflatable cylinder, and said pump, and an inflation fluid, said pump being selectively actuated by a user to inflate said inflatable cylinder with said inflation fluid, said lockout valve preventing inadvertent auto-inflation of said inflatable cylinder, said method comprising the steps of:

providing a pressure-responsive lockout valve including a valve body having an inlet port, an outlet port, a valve member, and a valve seat, a flow aperture formed in the valve body for flow of the fluid between the inlet port and the outlet port, a chamber formed between the flow aperture and the outlet port, the chamber having a surface that is movable in response to at least a threshold level of negative pressure applied at the outlet port, said valve member being movable between a closed position in sealing contact with said valve seat and an open position, such that when the pump is selectively actuated by the user to produce at least the threshold level of negative internal pressure at said outlet port, the negative internal pressure causes the movable surface of the chamber to deflect, causing the movable surface to contact the valve member, thereby causing said valve member to move to said open position and permitting the inflation fluid to flow from the reservoir through said pressure-responsive lockout valve to the inflatable cylinder;

opening at least a portion of the conduit; and operatively connecting said pressure-responsive lockout valve to said conduit at said opening such that said inlet port is connected in fluid communication with the conduit in a direction leading to the reservoir and said outlet port is connected in fluid communication with the conduit in a direction leading to the pump.

28. The method of claim 27 wherein the step of opening the conduit is accomplished by cutting the conduit to form a pair of free ends thereof, and wherein the step of operatively connecting the pressure-responsive lockout valve to the conduit is accomplished by connecting the inlet port to a one of said pair of free ends connected in fluid communication with the reservoir and the outlet port an opposing one of said pair of free ends connected in fluid communication with the pump.

29. The method of claim 28 wherein the step of operatively connecting the pressure-responsive lockout valve to the conduit is accomplished by splicing the pressure-responsive lockout valve to the pair of free ends of the conduit using connectors.

30. The method of claim 28 wherein the pressure-responsive lockout valve has a pair of tubing segments extending therefrom connected in fluid communication with the inlet port and the outlet port, and the step of operatively connecting the pressure-responsive lockout valve to the conduit is accomplished by splicing said pair of tubing segments extending from the pressure-responsive lockout valve to the pair of free ends of the conduit using connectors.

31. A lockout valve for controlling the flow of a fluid, said lockout valve comprising:

a valve body defining an inlet port and an outlet port, an interior chamber in fluid communication with the outlet port, and a movable surface, a valve seat disposed on said valve body, the valve seat defining an aperture; and a valve member mounted for movement relative to the valve seat, said valve member being movable between a closed position in sealing contact with said valve seat and an open position, said valve member sealingly contacting said valve seat and preventing the flow of the fluid through the lockout valve in response to positive fluid pressure applied at said inlet port, said valve member moving to said open position in response to a force exerted by a negative internal pressure applied at the outlet port that causes the movable surface to move inwardly into the interior chamber and contact the valve member and open the aperture, thereby permitting the fluid to flow from the inlet port through the aperture in the valve seat, the interior chamber, and the outlet port.

32. The lockout valve of claim 31 wherein the poppet moves axially relative to the valve seat generally parallel to a longitudinal axis, and the diaphragm is generally circular having a center point, said center point being generally aligned with said longitudinal axis along which the poppet moves axially.

33. The lockout valve of claim 31 wherein the poppet has a head, a tail, and a shaft, said head and said tail each being disposed on opposing ends of said shaft and opposing sides of the valve seat such that said shaft extends at least partially through the aperture, said tail of the poppet confrontingly contacting the valve seat and sealing the aperture when the poppet is in the closed position.

34. The lockout valve of claim 31 wherein the poppet has a head, a tail, and a shaft, said head and said tail each being disposed on opposing ends of said shaft and opposing sides of the valve seat such that said shaft extends at least partially through the aperture, the lockout valve including a bias member that exerts a spring force to bias said head of the poppet away from the valve seat.

35. The lockout valve of claim 34 wherein the bias member includes a plurality of flexible tines extending from the valve body and contacting the head of the poppet.

36. The lockout valve of claim 31 wherein the lockout valve includes a bias member that exerts a spring force to bias the poppet toward the closed position.

37. The lockout valve of claim 36 wherein the bias member includes a plurality of flexible tines extending from the valve body and contacting the poppet.

38. The lockout valve of claim 31 wherein the lockout valve includes a bias member that exerts a spring force to bias the valve member toward the closed position.

39. The lockout valve of claim 31 wherein the lockout valve is connected to a reservoir and a valve block having a check valve which opens at a predetermined threshold fluid pressure, and wherein the lockout valve permits the flow of fluid through the valve seat in a forward direction when fluid pressure from said reservoir is sufficiently less than said predetermined threshold fluid pressure, and the valve member moves to the closed position in sealing engagement with the valve seat at least when fluid pressure from said reservoir increases to said predetermined threshold fluid pressure.

40. The lockout valve of claim 31 wherein at least the valve body and the valve seat are fabricated from an elastomer.

41. The lockout valve of claim 31 wherein the valve member is fabricated from a plastic.

42. A lockout valve for controlling the flow of a fluid between a fluid reservoir and an inflatable member in a penile prosthesis, the lockout valve comprising:

a valve body having an inlet port for fluid communication with the reservoir and an outlet port for fluid communication with the inflatable member;

a flow aperture formed in the valve body for flow of the fluid between the inlet port and the outlet port;

a valve member that is movable between a closed position in which the valve member prevents flow of the fluid through the flow aperture and an open position in which the valve member allows flow of fluid through the flow aperture;

a bias member mounted to exert a bias force that biases the valve member toward the closed position, thereby preventing flow of fluid through the flow aperture; and a chamber formed between the flow aperture and the outlet port, the chamber having a surface that is movable in response to at least a threshold level of negative pressure applied at the outlet port to exert a force that moves the valve member against the bias force and toward the open position, thereby allowing fluid to flow through the flow aperture.

43. The lockout valve of claim 42, wherein the movable surface of the chamber includes a flexible diaphragm that forms a portion of a wall of the chamber.

44. The lockout valve of claim 42, wherein the bias member includes a plurality of resiliently deformable members.

\* \* \* \* \*

UNITED STATES PATENT AND TRADEMARK OFFICE
CERTIFICATE OF CORRECTION

PATENT NO.    : 5,851,176
DATED         : DECEMBER 22, 1998
INVENTOR(S)   : STEVEN N. WILLARD

It is certified that error appears in the above-identified patent and that said Letters Patent is hereby corrected as shown below:

At Col. 10, line 44, please delete "off", and insert --of--.

Signed and Sealed this

Sixteenth Day of January, 2001

Attest:

Q. TODD DICKINSON

*Attesting Officer*    *Commissioner of Patents and Trademarks*